(12) United States Patent
Neumann

(10) Patent No.: US 11,688,504 B2
(45) Date of Patent: Jun. 27, 2023

(54) METHODS AND SYSTEMS FOR INFORMING FOOD ELEMENT DECISIONS IN THE ACQUISITION OF EDIBLE MATERIALS FROM ANY SOURCE

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 16/699,616

(22) Filed: Nov. 30, 2019

(65) Prior Publication Data
US 2021/0166130 A1   Jun. 3, 2021

(51) Int. Cl.
*G16H 20/60* (2018.01)
*G06N 3/08* (2023.01)
(Continued)

(52) U.S. Cl.
CPC ......... *G16H 20/60* (2018.01); *G06F 18/2155* (2023.01); *G06F 18/24147* (2023.01);
(Continued)

(58) Field of Classification Search
CPC ...... G06N 3/088; G16H 20/60; G06K 9/6259; G06K 9/6278; G06Q 50/22; G06G 50/24
See application file for complete search history.

(56) References Cited

U.S. PATENT DOCUMENTS

| 9,659,225 B2 | 5/2017 | Joshi et al. |
| 10,360,495 B2 | 7/2019 | Chapela et al. |

(Continued)

FOREIGN PATENT DOCUMENTS

| WO | 2018204763 | 11/2018 |
| WO | 2019166357 | 9/2019 |
| WO | 2019183404 | 9/2019 |

OTHER PUBLICATIONS

Plis et al., "A Machine Learning Approach to Predicting Blood Glucose Levels for Diabetes Management," Modern Artificial Intelligence for Health Analystics: Papers from the AAAI-14 (Year: 2014).*

(Continued)

*Primary Examiner* — Ann J Lo
*Assistant Examiner* — Van C Mang
(74) *Attorney, Agent, or Firm* — Caldwell Intellectual Property Law

(57) ABSTRACT

A system for informing food element decisions in the acquisition of edible materials from any source. The system includes a processor coupled to a memory configured to receive from a user client device a food element descriptor uniquely identifying a particular food element. The system retrieves from a physiological database at least an element of physiological data. The system identifies using at least an element of physiological data and a machine-learning algorithm user constitutional enhancing food elements and user constitutional advancing food elements. The system classifies using a food element classifier a food element descriptor. The system displays on a graphical user interface a constitutional enhancing food element or a constitutional advancing food element.

18 Claims, 9 Drawing Sheets

(51) Int. Cl.
  *G06V 10/24*    (2022.01)
  *G06N 3/088*    (2023.01)
  *G06F 18/214*   (2023.01)
  *G06F 18/2413*  (2023.01)
  *G06F 18/2415*  (2023.01)

(52) U.S. Cl.
  CPC ....... *G06F 18/24155* (2023.01); *G06N 3/088* (2013.01); *G06V 10/245* (2022.01)

(56) References Cited

U.S. PATENT DOCUMENTS

| | | | |
|---|---|---|---|
| 10,361,003 B2 | 7/2019 | Segal et al. | |
| 10,380,325 B2* | 8/2019 | Apte | G16B 99/00 |
| 2003/0087320 A1* | 5/2003 | Vojdani | G01N 33/53 |
| | | | 435/7.31 |
| 2016/0232311 A1* | 8/2016 | Segal | G16H 50/20 |
| 2017/0061821 A1 | 3/2017 | Choi et al. | |
| 2019/0228856 A1 | 7/2019 | Leifer et al. | |
| 2019/0295440 A1* | 9/2019 | Hadad | G16H 20/60 |
| 2019/0325498 A1 | 10/2019 | Clark | |
| 2019/0333624 A1 | 10/2019 | Huang | |

OTHER PUBLICATIONS

Erban et al., "Discovery of food identity markers by metabolomics and machine learning technology" 2019 (Year: 2019).*
Brandon, John, "Instacart AI helps personal shoppers buy groceries faster," venturebeat.com, Jul. 12, 2017.

* cited by examiner

METHODS AND SYSTEMS FOR INFORMING FOOD ELEMENT DECISIONS IN THE ACQUISITION OF EDIBLE MATERIALS FROM ANY SOURCE

FIELD OF THE INVENTION

The present invention generally relates to the field of artificial intelligence. In particular, the present invention is directed to methods and systems for informing food element decisions in the acquisition of edible materials from any source.

BACKGROUND

Frequently knowing what food elements to acquire in a grocery store can lead to sensory overload. Trying to understand labels and how a particular food element may impact one's body can be challenging if not impossible. This can be further complicated by each individual's response to a food element that is unique and may not be characteristic of others.

SUMMARY OF THE DISCLOSURE

In an aspect, a system for informing food element decisions in the acquisition of edible materials from any source. The system includes a processor coupled to a memory and configured to receive from a user client device operated by a user a food element descriptor wherein the food element descriptor further comprises a sequence uniquely identifying a particular food element. The processor is further configured to retrieve from a physiological database located on the processor at least an element of user physiological data. The processor is further configured to identify using the at least an element of user physiological data and a machine-learning algorithm user constitutional enhancing food element and user constitutional advancing food element. The processor is further configured to classify using a food element classifier the food element descriptor as a function of the identified user constitutional enhancing food element and user constitutional advancing food element. The processor is further configured to display on a graphical user interface located on the processor the constitutional enhancing food element or the constitutional advancing food element.

In an aspect, a method of informing food element decisions in the acquisition of edible materials from any source. The method includes receiving by a processor from a user client device operated by a user a food element descriptor wherein the food element descriptor further comprises a sequence uniquely identifying a particular food element. The method includes retrieving by the processor from a physiological database located on the processor at least an element of user physiological data. The method includes identifying by the processor using the at least an element of user physiological data and a machine-learning algorithm user constitutional enhancing food element and user constitutional advancing food element. The method includes classifying by the processor using a food element classifier the food element descriptor as a function of the identified user constitutional enhancing food element and user constitutional advancing food element. The method includes displaying by the processor on a graphical user interface located on the processor the constitutional enhancing food element or the constitutional advancing food element.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for informing food element decisions in the acquisition of edible materials from any source. In an embodiment, such decisions about what to acquire in regards to edible materials can have a lasting effect on a user's constitution and either help or harm a user in achieving vibrancy and longevity.

Figure 1:
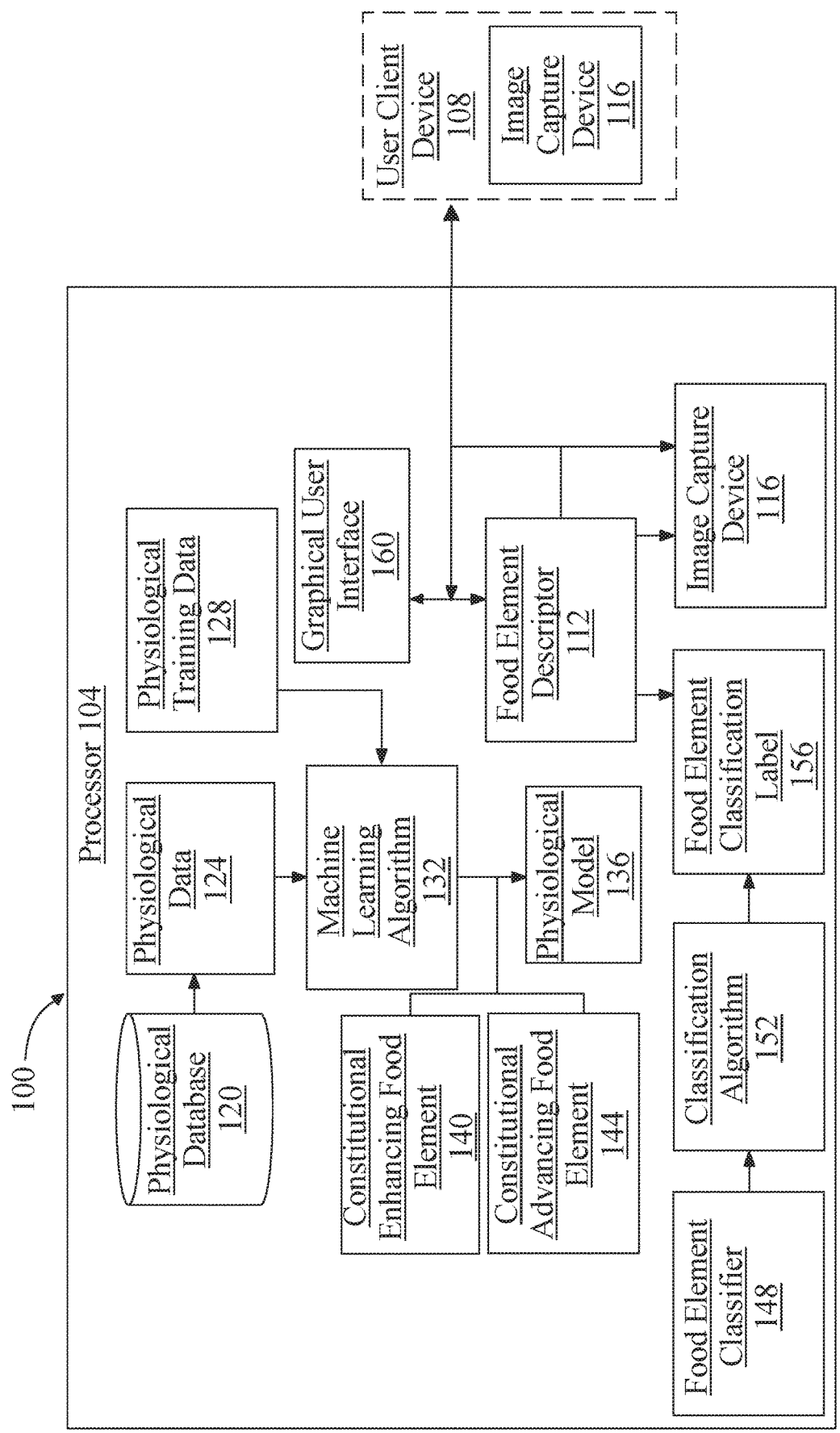
FIG. 1 is a block diagram illustrating an exemplary embodiment of a system for informing food element decisions in a grocery store.

Referring now to FIG. 1, an exemplary embodiment of a system 100 for informing food element decisions in the acquisition of edible materials is illustrated. System 100 includes a processor coupled to a memory. Processor 104 may include any processor 104 as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single processor operating independently or may include two or more processor operating in concert, in parallel, sequentially or the like; two or more computing devices may be included together in a single processor 104 or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof.

Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a processor 104. Processor 104 may include but is not limited to, for example, a processor or cluster of computing devices in a first location and a second processor or cluster of computing devices in a second location. Processor 104 may include one or more computing devices dedicated to data storage, security, distribution of traffic for load balancing, and the like. Processor 104 may distribute one or more computing tasks as described below across a plurality of computing devices of processor 104, which may operate in parallel, in series, redundantly, or in any other manner used for distribution of tasks or memory between computing devices. Processor 104 may be implemented using a "shared nothing" architecture in which data is cached at the worker; in an embodiment, this may enable scalability of system 100 and/or processor 104.

Still referring to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 is configured to receive, from a user client device 108 operated by a user, a food element descriptor 112. User client device 108 may include without limitation, a display in communication with processor 104, where a display may include any display as described herein. User client device 108 may include an additional computing device, such as a mobile device, laptop, desktop, computer and the like. User client device 108 may transmit and/or receive one or more inputs from processor 104 utilizing any network methodology as described herein. User client device 108 may be operated by a user which may include any human subject.

With continued reference to FIG. 1, processor 104 receives a food element descriptor 112. A "food element descriptor 112" as used in this disclosure, includes any identifier of a food element. An identifier may include a specific sequence of characters, numbers, letters, and/or words that may identify a particular food element. An identifier may include a picture or photograph of a particular food element. An identifier may include a globally recognized uniform identifier such as a uniform code commission (UCC) barcode. Processor 104 includes an image capture device 116. An "image capture device 116" as used in this disclosure, includes any device suitable to take a picture or photograph of a food element and/or food element descriptor 112. Image capture device 116 may include for example a camera, mobile phone camera, scanner or the like. Food element descriptor 112 may include image capture using an image capture device 116 located on user client device 108 such as a mobile phone camera. For example, a user may take a photograph of a food element descriptor 112 using a camera located on user client device 108 containing an image capture that contains a photograph of a UCC barcode or a photograph that contains a picture of a particular food such as a picture of an eggplant or a picture of a boxed pasta. A "food element" as used in this disclosure, includes any substance intended for consumption by a human being. A food element may include a substance containing a single ingredient such as an avocado or lamb meat. A food element may include a substance containing two or more ingredients such as a quinoa salad containing chickpeas, red onion, red pepper, and shrimp. A food element may include a prepackaged substance such as RITZ CRACKERS as produced by Nabisco of East Hanover, N.J. or PUFFED MILLET CEREAL as produced by Arrowhead Mills of Hereford, Tex. A food element may include a generic brand that may not contain a brand name such as a particular grocery store or food store brand label or private label. A food element may include a brand name product such as 365 EVERYDAY VALUE PRODUCTS as produced by Whole Foods Market of Austin. A food element may include any substance available for physical and/or digital sale. Physical sale may include but is not limited to a grocery store, food store, supermarket, bazaar, bodega, co-op, corner store, delicatessen, general store, trading post, warehouse, food hall, market, kitchen, retail store, outpost and the like. Digital sale may include but is not limited to any food element sold through a digital media such as a website, blog, social media platform, digital magazine, digital property and the like. Digital may include but is not limited to an individual food element such as an avocado available for purchase on a website. Digital may include but is not limited to a combination of one or more food elements available for purchase such as a meal containing multiple food elements such as chicken alfredo with broccoli.

With continued reference to FIG. 1, a food element may be transformed into a vector containing a listing of one or more ingredients contained within a food element. In an embodiment, a processor 104 may generate an optimal vector output that may include one or more vector outputs that may generate a desired outcome to contain beneficial ingredients. Processor 104 may select one or more ingredients that may be placed on a vector output based on a threshold importance score of ingredients based on user body information. In an embodiment, vector output may include one or more constitutional enhancing food elements and/or one or more constitutional advancing food elements as described below in more detail. In such an instance, a vector that contains one or more ingredients that may not be important for a user's body may cluster to one particular group as described below as compared to a vector that may contain one or more ingredients that may be important for a user's body. A first vector output is n n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of priorities, and/or is to be compared to such a weighing of priorities. Priorities may be generated based on user input, where a user may prefer a particular attribute.

With continued reference to FIG. 1, one or more vector outputs may be utilized to generate one or more clustering algorithms. Clustering algorithms may include any of the clustering algorithms as described here. This may include for example, a k-nearest neighbors algorithm, a k-means clustering algorithm, a hierarchical clustering algorithm and the like.

With continued reference to FIG. 1, system 100 may include a graphical user interface 160 which may be located on processor 104. Graphical user interface may include without limitation a form or other graphical element having data entry fields, wherein a user may select one or more food elements from a list displayed on graphical user interface. For instance and without limitation, graphical user interface may display a list of one or more food elements organized into categories such as vegetables, proteins, fats, fruits, grains, herbs, spices, beverages, processed foods, canned goods, and miscellaneous. For example, vegetable category may include a list of vegetables that a user may select one or more of such as tomato, onion, chilies, peppers, cucumber, cabbage, eggplant, carrot, turnip, lettuce, spinach, and kale. Graphical user interface may include free form entry fields such as text entry fields where a user may be able to type or otherwise enter text enabling a user to type in a particular food element that may not be contained on a displayed list. Graphical user interface may include an option for a user to upload a photograph of one or more food items. Graphical user interface may include an option for a user to upload a picture of a food item identifier such as a photograph of a uniform code commission barcode.

With continued reference to FIG. 1, processor 104 is configured to retrieve from a physiological database 120 located on processor 104 at least an element of user physiological data 124. Physiological database 120 may be implemented, without limitation, as a relational database, a key-value retrieval datastore such as a NOSQL database, or any other format or structure for use as a datastore that a person skilled in the art would recognize as suitable upon review of the entirety of this disclosure. Physiological database 120 may store one or more elements of user physiological data 124. As used in this disclosure, "user physiological data 124" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data 124 describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data 124 may include, without limitation any result of any medical test, physiological assessment, cognitive assessment, psychological assessment, or the like. System 100 may receive at least a physiological data 124 from one or more other devices after performance; system 100 may alternatively or additionally perform one or more assessments and/or tests to obtain at least a physiological data 124, and/or one or more portions thereof, on system 100. For instance, at least physiological data 124 may include or more entries by a user in a form or similar graphical user interface 160 object; one or more entries may include, without limitation, user responses to questions on a psychological, behavioral, personality, or cognitive test. For instance, processor 104 may present to user a set of assessment questions designed or intended to evaluate a current state of mind of the user, a current psychological state of the user, a personality trait of the user, or the like; processor 104 may provide user-entered responses to such questions directly as at least a physiological data 124 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data 124 may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data 124 may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, Entamoeba histolytica, fecal lactoferrin, Giardia lamblia EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *clostridium difficile, cryptosporidium* species, *Cyclospora cayetanensis, Cryptosporidium EIA, Dientamoeba fragilis, Entamoeba histolytica, Escherichia coli, Entamoeba histolytica, Giardia, H. pylori, candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, Bacteroides vulgates', Bacteroides-Prevotella, Barnesiella species, Bifidobacterium longarm, *Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. helicobacter pylori breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor.

Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data 124 may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data 124 may be obtained from a physically extracted sample. A physical sample may include a signal from a sensor configured to detect physiological data 124 of a user and record physiological data 124 as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, processor 104 is configured to identify using at least an element of user physiological data 124 a plurality of constitutional effect labels. "Constitutional effect labels" as used in this disclosure, include an indicator of either a positive or negative effect on a user's constitution. A user's constitution includes a user's current health status. Plurality of constitutional effect labels may include a plurality of user constitutional enhancing food elements 140 and a plurality of user constitutional advancing food elements 132. A "constitutional enhancing food element 140" as used in this disclosure, includes any food element that is beneficial for a particular human being. A beneficial food element may include a food element that promotes or sustains good health. A beneficial food may provide one or more nutrients that a user may require to sustain life. Nutrients may include protein, carbohydrates, fat, water, vitamins, minerals and the like. A beneficial food may contribute to a user's overall health and longevity. A beneficial food may help a user in achieving and/or maintaining good health. Good health may include a medical state of a user where a user is free of disease, reverses disease and/or has achieved remission of one or more disease states. For example, good health may be achieved by a user who achieves remission of rheumatoid arthritis or a user who reverses prediabetes and maintains blood sugar levels within normal range. A "constitutional advancing food element 144" as used in this disclosure, includes any food element that advances a progression toward a negative health outcome. A food element that advances a progression toward a negative health outcome may include a food element that does not promote or sustain good health. A food element that is not beneficial may contribute to advancing a particular disease state, premature aging, may be incompatible with a user's constitution, and/or may detract from a user's vibrant constitution. A food element that is not beneficial may not help a user in achieving a state where a user is free of disease, may contribute to disease progression, and/or may not help a user in achieving disease remission. A food element that is not beneficial may be incompatible with a user's constitution. For instance and without limitation, a food element such as coconut oil may be incompatible with a user who has at least one copy of the apolipoprotein E4 genetic variation (APOE4) while coconut oil may be compatible with a user who has two copies of the apolipoprotein E3 genetic variation (APOE3).

With continued reference to FIG. 1, processor 104 identifies user constitutional enhancing food element 140 or user constitutional advancing food element 144 by receiving physiological training data 128. Physiological training data 128 includes a plurality of pairs of physiological data 124 sets and constitutional enhancing food element 140 and constitutional advancing food element 144. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithm and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithm, and/or automated association of data in the data entry with descriptors or into a given format. The ability to categorize data entries automatedly may enable the same training data to be made applicable for two or more distinct machine-learning algorithm 132 as described in further detail below. Training data used by processor 104 may correlate any input data as described in this disclosure to any output data as described in this disclosure.

With continued reference to FIG. 1, processor 104 is configured to generate using a machine-learning algorithm 132 and physiological training data 128 a physiological model 136 correlating physiological data 124 with constitutional enhancing food element 140 and constitutional advancing food element 144. A machine learning process, also referred to as a machine-learning algorithm 132, is a process that automatedly uses training data and/or a training set as described above to generate an algorithm that will be performed by a processor 104 and/or module to produce outputs given data provided as inputs; this is in contrast to a non-machine learning software program where the commands to be executed are determined in advance by a user and written in a programming language.

Continuing to refer to FIG. 1, machine-learning algorithm 132 may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithm 132 may include, without limitation, linear discriminant analysis. Machine-learning algorithm 132 may include quadratic discriminate analysis. Machine-learning algorithm 132 may include kernel ridge regression. Machine-learning algorithm 132 may include support vector machines, including without limitation support vector classification-based regression processes. Machine-learning algorithm 132 may include stochastic gradient descent algorithms, including classification and regression algorithms based on stochastic gradient descent. Machine-learning algorithm 132 may include nearest neighbors algorithms. Machine-learning algorithm 132 may include Gaussian processes such as Gaussian Process Regression. Machine-learning algorithm 132 may include cross-decomposition algorithms, including partial least squares and/or canonical correlation analysis. Machine-learning algorithm 132 may include naïve Bayes methods. Machine-learning algorithm 132 may include algorithms based on decision trees, such as decision tree classification or regression algorithms. Machine-learning algorithm 132 may include ensemble methods such as bagging meta-estimator, forest of randomized tress, AdaBoost, gradient tree boosting, and/or voting classifier methods. Machine-learning algorithm 132 may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithm 132 may include unsupervised machine-learning algorithm. Supervised machine learning algorithm, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithm that may be used to determine relation between inputs and outputs.

With continued reference to FIG. 1, supervised machine-learning processes may include classification algorithm, defined as processes whereby a processor 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithm may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, machine learning processes may include lazy learning processes. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. A lazy-learning process may include any suitable "lazy learning" algorithm, including without limitation a K-nearest neighbors algorithm, a lazy naive Bayes algorithm, or the like. Persons skilled in the art, upon reviewing the entirety of this disclosure, will be aware of various lazy-learning algorithms that may be applied to generate outputs as described in this disclosure, including without limitation lazy learning applications of machine-learning algorithm 132 as described in further detail below.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, processor 104 is configured to generate using a machine-learning algorithm 132 and physiological training data 128 a physiological model 136 correlating physiological data 124 with constitutional enhancing food elements and constitutional advancing food element 144. Machine-learning algorithm 132 may include any of the machine-learning models as described above. This may include for example, one or more unsupervised machine-learning algorithm, one or more unsupervised machine-learning algorithm, and/or one or more lazy-learning algorithms.

With continued reference to FIG. 1, processor 104 is configured to classify using a food element classifier 148 a food element identifier as a function of identified user constitutional enhancing food element 140 or user constitutional advancing food element 144. Food element classifier 148 may generate a classification algorithm 152, defined as a process whereby a processor 104 may generate a classification algorithm 152 and may derive from training data a model for sorting inputs into categories or bins of data. Food element classifier 148 includes any machine-learning model generated using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Processor 104 may utilize a food element descriptor 112 as an input and output a user constitutional enhancing food element 140 classification label or a user constitutional advancing food element 144 classification label. Processor 104 identifies using the classification algorithm 152 the food element descriptor 112 as a user constitutional enhancing food element 140 or a user constitutional advancing food element 144.

With continued reference to FIG. 1, classification algorithm 152 may include generating a Naïve Bayes classification algorithm. Naive Bayes classification algorithm generates classifiers by assigning class labels to problem instances, represented as vectors of feature values. Class labels are drawn from a finite set. Naïve Bayes classification algorithm may include generating a family of algorithms that assume that the value of a particular feature is independent of the value of any other feature, given a class variable. Naïve Bayes classification algorithm may be based on Bayes Theorem expressed as $P(A/B)=P(B/A)P(A)\div P(B)$, where $P(A/B)$ is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming classification training data into a frequency table. Processor 104 may then calculate a likelihood table by calculating probabilities of different data entries and classification labels. Processor 104 utilizes a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when feature vectors are binary. Naïve Bayes classification algorithm utilizes classification training data and a user physiological data 124 as an input to output a classification label. A "classification label" as used in this disclosure, includes a label that indicates whether an input belongs to a particular class or not. In an embodiment, a classification label may include an indication as to whether a particular food element descriptor 112 is considered a user constitutional enhancing food element 140 or a user constitutional advancing food element 144.

With continued reference to FIG. 1, classification algorithm 152 may include generating a K-nearest neighbor (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n}a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user-entered words and/or phrases, a plurality of attributes of a media item, such as spoken or written text, objects depicted in images, metadata, or the like, to clusters representing themes.

With continued reference to FIG. 1, processor 104 is configured to display on a graphical user interface 160 located on processor 104 the classified constitutional enhancing or constitutional advancing food element descriptor. Processor 104 may display on a graphical user interface 160 utilizing any network methodology as described herein. Graphical user interface 160 includes any of the graphical user interfaces as described above.

Figure 2:
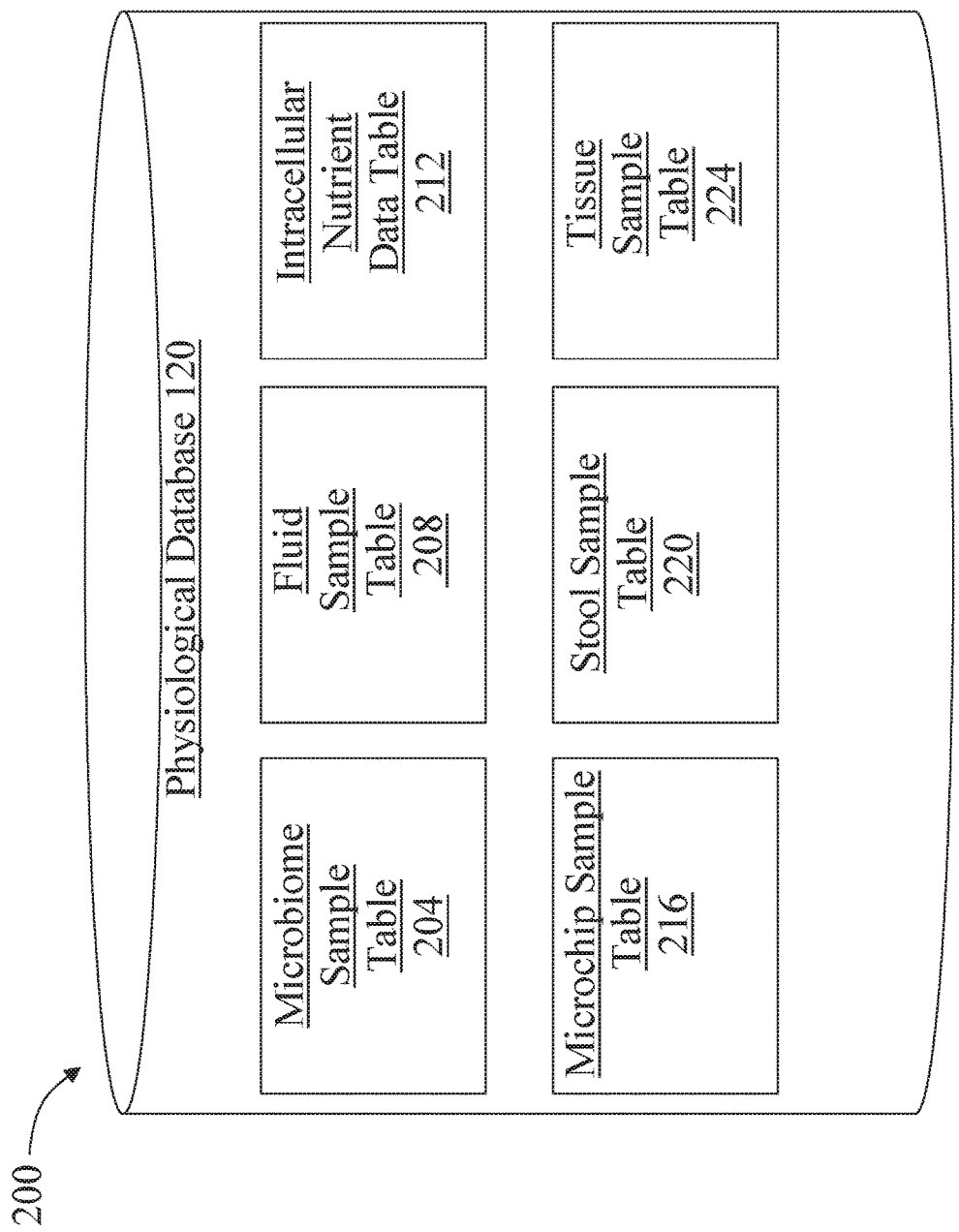
FIG. 2 is a block diagram illustrating an exemplary embodiment of a physiological database.

Referring now to FIG. 2, an exemplary embodiment of physiological database 120 is illustrated. Physiological database 120 may be implemented as a data structure as described above in reference to FIG. 1. Physiological database 120 may include one or more elements of physiological data 124 pertaining to a particular user. Physiological data 124 contained within physiological database 120 may be organized according to type of biological extraction utilized to analyze a particular element of physiological data, body system or body dimension that a particular element of physiological data 124 pertains to, sample type, category of physiological data 124 and the like. One or more tables contained within physiological database 120 may include microbiome sample table 204; microbiome sample table 204 may contain one or more elements of physiological data 124 containing a microbiome sample. For instance and without limitation, microbiome sample table 204 may contain an element of physiological data 124 such as a stool sample analyzed for levels of pathogenic bacteria. One or more tables contained within physiological database 120 may include fluid sample table 208; fluid sample table 208 may contain one or more elements of physiological data 124 containing a fluid sample. For instance and without limitation, fluid sample table 208 may include a saliva sample analyzed for one or more hormone levels. One or more tables contained within physiological database 120 may include intracellular nutrient data table 212; intracellular nutrient data table 212 may include one or more elements of physiological data 124 containing an intracellular nutrient level. For instance and without limitation, intracellular nutrient data table 212 may include an intracellular level of Vitamin C. One or more tables contained within physiological database 120 may include microchip sample table 216; microchip sample table 216 may include one or more elements of physiological data 124 obtained from a microchip. For instance and without limitation, microchip sample table 216 may include one or more extracellular nutrient levels of coenzyme Q 10 obtained from a microchip embedded under the skin. One or more tables contained within physiological database 120 may include stool sample table 220; stool sample table 220 may include one or more elements of physiological data 124 obtained from a stool sample. For instance and without limitation, stool sample table 220 may include a measurement of a stool pH level. One or more tables contained within physiological database 120 may include tissue sample table 224; tissue sample table 224 may include one or more elements of physiological data 124 obtained from a tissue sample. For instance and without limitation, tissue sample table 224 may include an intestinal biopsy analyzed for the presence or absence of Celiac disease.

Figure 3A:
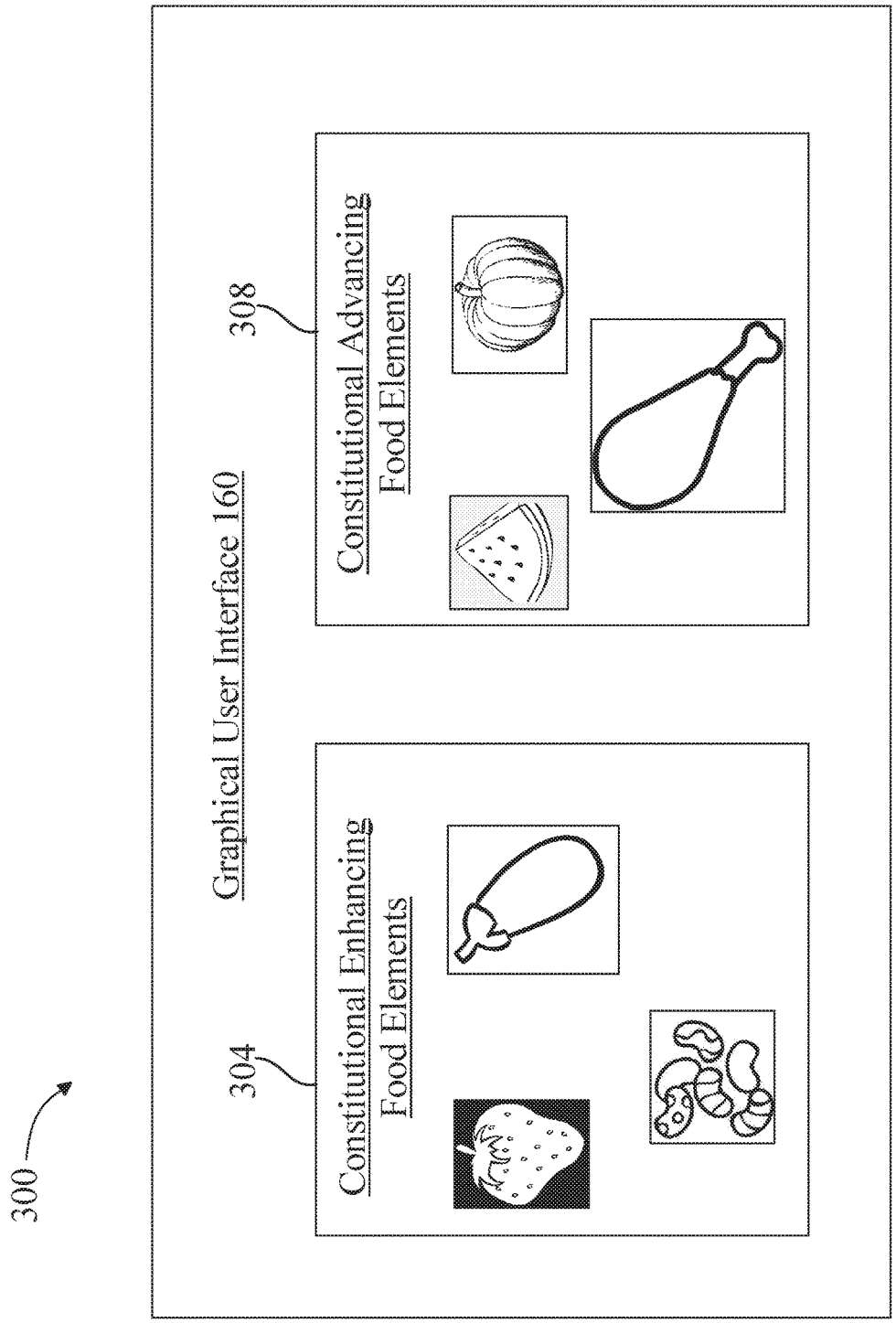
FIGS. 3A-3D are a diagrammatic representation of various graphical user interfaces.
Figure 3B:
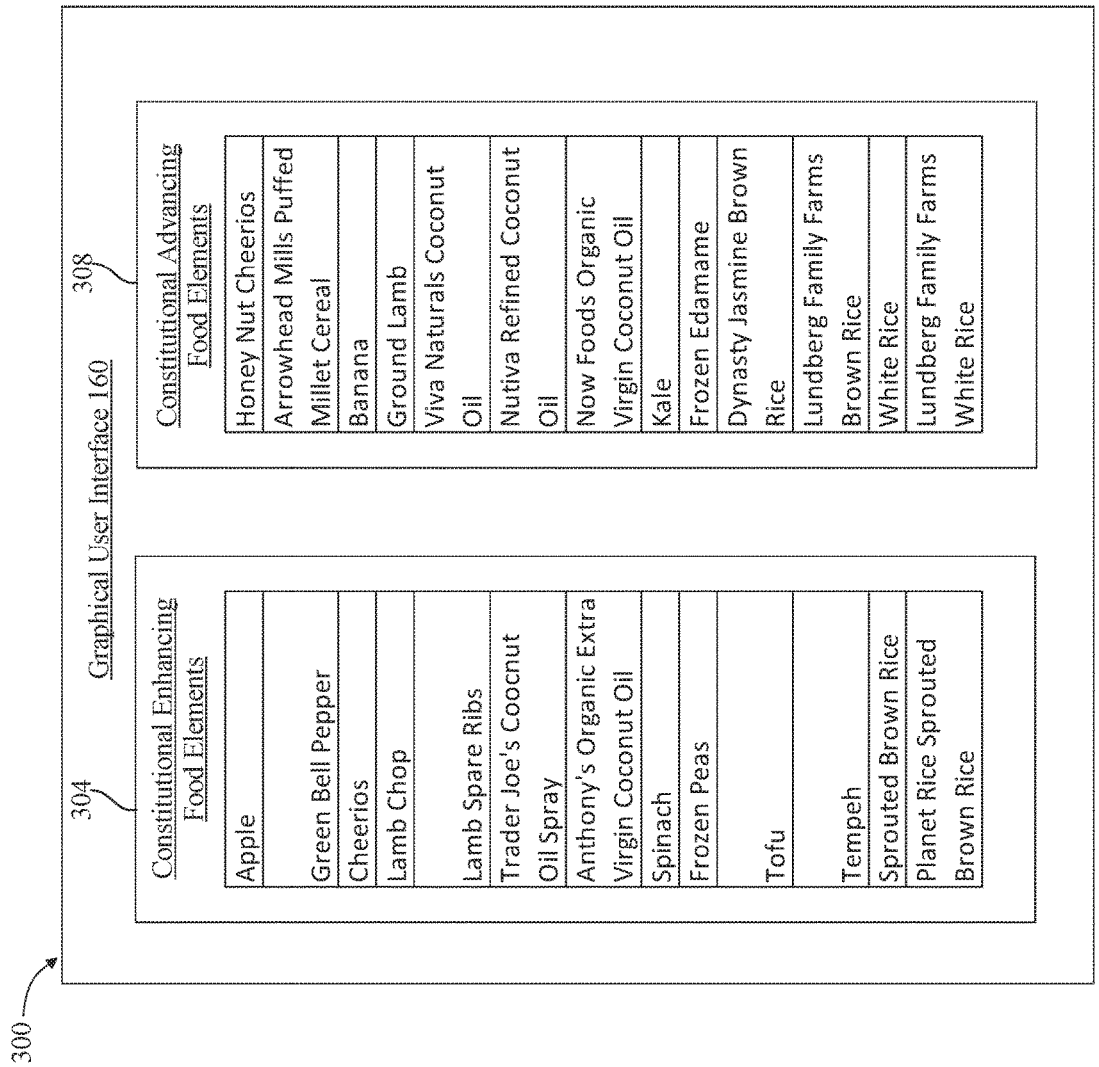

Referring now to FIGS. 3A-3D, an exemplary embodiment of graphical user interface 160 is illustrated. Graphical user interface 160 may display one or more constitutional enhancing food elements 140 and/or one or more constitutional advancing food element 144. Alternatively or additionally, one or more constitutional enhancing food elements and/or one or more constitutional advancing food elements may be transmitted to user client device 108 utilizing any network methodology as described herein. In FIG. 3A, one or more constitutional enhancing food elements 304 may be displayed on graphical user interface 160 illustrating a picture of one or more constitutional enhancing food elements 304. For example, graphical user interface 160 may display several constitutional enhancing food element 304 that include strawberries, eggplant, and black beans. One or more constitutional advancing food elements 308 may be displayed on graphical user interface 160 illustrating a picture of one or more constitutional advancing food element 308. For example, graphical user interface 160 may display several constitutional advancing food elements 308 that include watermelon, pumpkin, and chicken drumsticks. In FIG. 3B, one or more constitutional enhancing food elements 304 may be displayed on graphical user interface 160 containing a textual display of one or more constitutional enhancing food elements 304. For example, textual display may include a generic identifier of one or more constitutional enhancing food elements 304 such as apple or green bell pepper. Textual display includes a specific brand name of one or more constitutional enhancing food elements 304 such as Trader Joe's Coconut Oil Spray or Anthony's Organic Extra Virgin Coconut Oil. Textual display may include a specific form of one or more constitutional enhancing food element 304 such as sprouted brown rice as compared to brown rice and a lamb chop and lamb spareribs as compared to ground lamb. Textual display may include a specific form and brand name of one or more constitutional enhancing food element 304 such as planet rice sprouted brown rice. One or more constitutional advancing food element 308 may be displayed on graphical user interface 160 containing a textual display of one or more constitutional advancing food element 308. For example, textual display may include a generic identifier of one or more constitutional advancing food element 308 such as banana or white rice. Textual display may include a specific brand name of one or more constitutional advancing food element 308 such as honey nut cheerios or arrowhead mills puffed millet cereal. Textual display may include a specific form of one or more constitutional advancing food element 308 such as ground lamb as opposed to a lamb chop or lamb spare ribs as well as Nutiva refined coconut oil as compared to other forms of coconut oil such as virgin coconut oil or nonrefined coconut oil as week as frozen edamame as compared to fresh edamame. Textual display may include a specific form and brand name of one or more constitutional advancing food element 308 such as now foods organic virgin coconut oil.

Figure 3C:
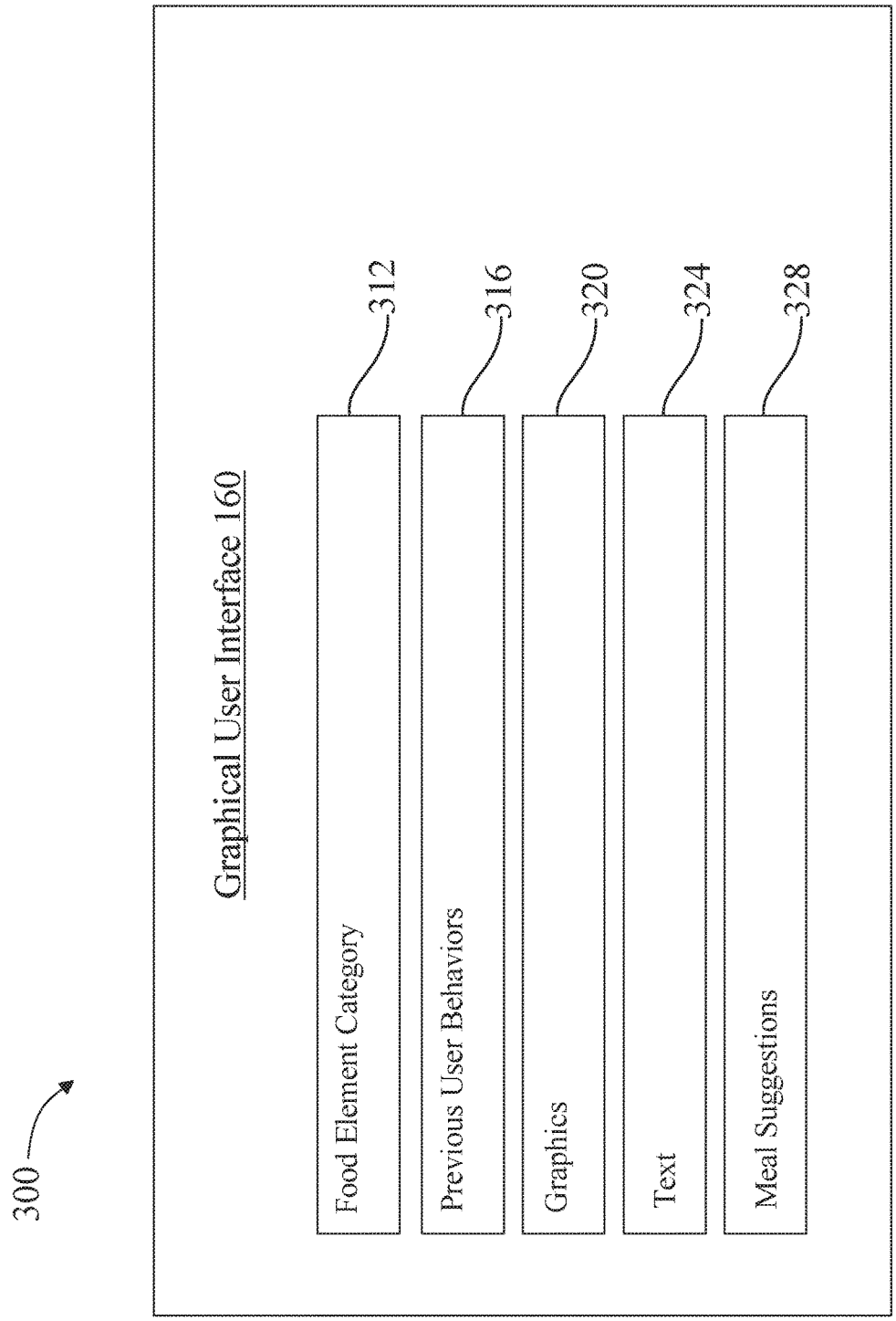
Figure 3D:
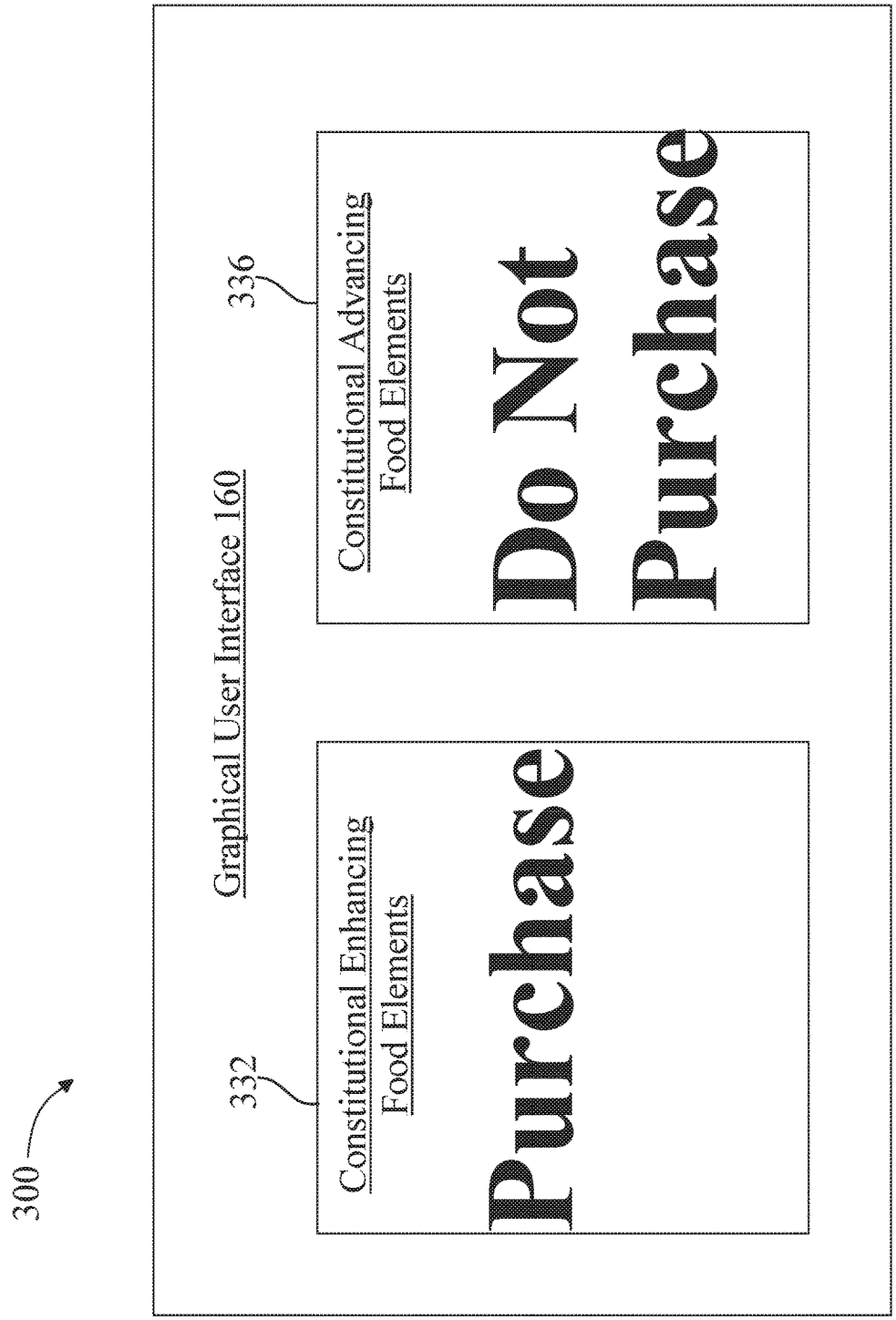

With continued reference to FIG. 3, in FIG. 3C graphical user interface 160 may display one or more options as to how particular information may be displayed to a user. Information displayed to user on graphical user interface 160 may be selected by a user. One or more options may include displaying constitutional enhancing food elements and/or constitutional advancing food element 144 by a food element category 312. Food element category 312 may include one or more categories of food elements that may be displayed to a user. Food element category 312 may include one or more food elements that share common traits. Food element category 312 may include categories such as vegetables, proteins, fats, fruits, grains, herbs, spices, beverages, processed foods, canned goods, and miscellaneous. In an embodiment, a user may select one or more categories that may display constitutional enhancing food element 304 and/or constitutional advancing food element 308 of food elements in one or more categories. For example, a user may select a food element category such as vegetables whereby graphical user interface 160 may display constitutional enhancing food element 140 that include vegetables such as alfalfa sprouts, artichoke, brussels sprouts, and endive. In such an instance, graphical user interface 160 may display constitutional advancing food element 144 that include vegetables such as Jerusalem artichoke, kale, sauerkraut, broccoli, beet, and asparagus. One or more options on graphical user interface 160 may include previous user behaviors 316. Previous user behaviors 316 may include previous food element descriptor 112 that may have been received from system 100 from user. For example, selection of previous user behaviors 316 by user may display previous food element descriptor 112 containing an indication as to whether they were determined to be constitutional enhancing food element 140 or constitutional advancing food element 144. One or more options on graphical user interface 160 may include graphics option 320. Graphics option 320 may include displaying constitutional enhancing food element 304 and/or constitutional advancing food element 308 as graphical or pictorial displays on graphical user interface 160 as described above in reference to FIG. 3A. one or more options on graphical user interface 160 may include text option 324. Text option 324 may include displaying constitutional enhancing food element 304 and/or constitutional advancing food element 308 as textual displays on graphical user interface 160 as described above in more detail in reference to FIG. 3B. One or more options on graphical user interface 160 may include meal suggestions 328. Meal suggestions 328 may include displaying meal suggestions to a user that contain constitutional enhancing food element 140 and that do not contain constitutional advancing food element 144. Referring now to FIG. 3D, graphical user interface 160 may display a textual output 332 that indicates that a user may purchase a particular food element that has been determined to be a constitutional enhancing food element 140. Graphical user interface 160 may display a textual output 336 that indicates that a user should not purchase a particular food element that has been determined to be a constitutional advancing food element 144.

Figure 4:
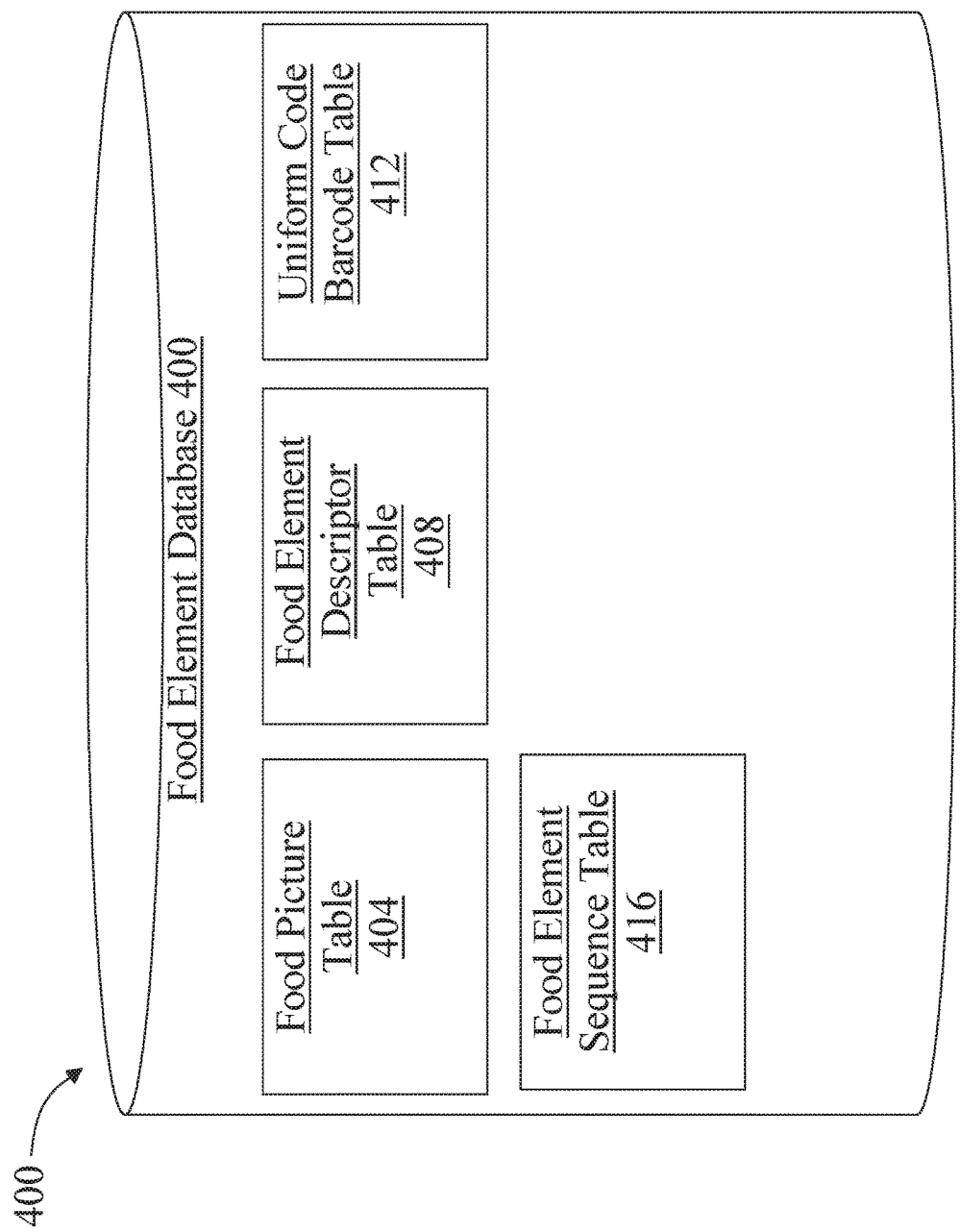
FIG. 4 is a block diagram illustrating an exemplary embodiment of a food element database.

Referring now to FIG. 4, an exemplary embodiment of a food element database 400 is illustrated. Food element database may be implemented as any data structure suitable for use as physiological database 120 as described above in reference to FIG. 1. Food element database may include one or more data tables containing one or more entries utilized to identify a particular food element. One or more tables contained within food element database 400 may include food picture table 404; food picture table 404 may include one or more data entries containing one or more pictures of a food element. One or more tables contained within food element database 400 may include food element descriptor table 408; food element descriptor table 408 may include one or more data entries containing one or more food element descriptor 112. One or more tables contained within food element database 400 may include uniform code barcode table 412; uniform code barcode table 412 may include one or more data entries containing one or more uniform code commission (UCC) barcodes. One or more tables contained within food element database 400 may include food element sequence table 416; food element sequence table 416 may include one or more sequences uniquely identifying a food element.

Figure 5:
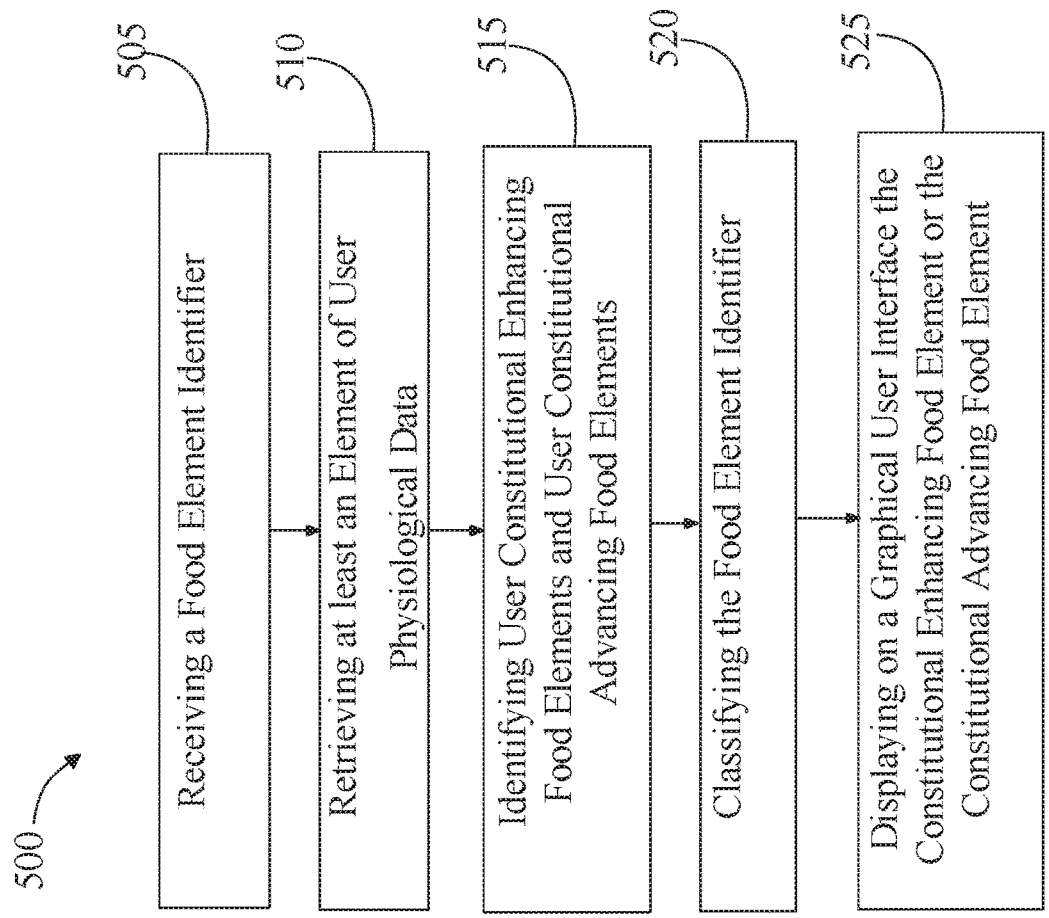
FIG. 5 is a process flow diagram illustrating an exemplary embodiment of a method of informing food element decisions in a grocery store.

Referring now to FIG. 5, an exemplary embodiment of a method 500 of informing food element decisions in a grocery store. At step 505 a processor 104 receives from a user client device 108 operated by a user a food element descriptor 112 wherein the food element descriptor 112 further comprises a sequence uniquely identifying a particular food element. Food element descriptor 112 includes any food element may include a specific sequence of characters, numbers, letters, and/or words that may identify a particular food element. For example, a food element descriptor 112 may include a name of a particular food element such as carrots or navel oranges. An identifier may include a picture or photograph of a particular food element. For example, an identifier may include a photograph of a food element such as an Italian eggplant. An identifier may include a globally recognized uniform identifier such as a uniform code commission (UCC) barcode that uniquely identifies a particular food element. Processor 104 may receive a food element descriptor 112 utilizing any network methodology as described herein. Processor 104 may receive at image capture device 116 a wireless transmission from a user client device 108 containing a picture of a food element. Image capture device 116 may include a camera, mobile phone camera, scanner or the like. For example, processor 104 may receive at image capture device 116 a transmission from a user client device 108 containing a picture of a seaweed salad. Processor 104 may receive at image capture device 116 a wireless transmission from user client device 108 containing a picture of a uniform code commission barcode. In an embodiment, image capture device 116 may be contained within user client device 108 and user may take a photograph of a uniform code commission barcode located on bananas using user client device 108. In such an instance, the photograph of the uniform code commission barcode located on bananas may be transmitted to processor 104 utilizing any network transmission as described herein.

With continued reference to FIG. 5, at step 510 a processor 104 retrieves from a physiological database 120 located on a processor 104 at least an element of user physiological data 124. In an embodiment, processor 104 may receive a user identifier transmitted from user client device 108. a "user identifier" as used in this disclosure, includes any data that uniquely identifies a particular user. Data may include a user's name, a user's date of birth, a user's medical identification number, a public and/or private key pair, a cryptographic hash, a biometric identifier such as an iris scan, fingerprint scan, a palm vein scan, a retina scan, facial recognition, DNA, a personal identification number, a driver's license or passport, token-based identification systems, digital signatures, and the like. Uniqueness may include uniqueness within system 100 such as ensuring that a particular user identifier is not already utilized by another user. Uniqueness may include a statistically ensured uniqueness such as a global unique identifier (GUID), or a unique identifier identification (UID). In an embodiment, processor 104 may compare a user identifier received from a user client device 108 to a user identifier that may be stored in a physiological database 120. Processor 104 may compare the user identifier received from a user client device 108 such as a fingerprint scan that uniquely identifies the user to a stored fingerprint scan of the user to ensure that both user identifiers match and are indicative of the same user. In such an instance, processor 104 may then proceed to retrieve an element of user physiological data 124 from physiological database 120. An element of user physiological data 124 may include any of the physiological data 124 as described above in reference to FIG. 1. For example and without limitation, an element of user physiological data may include a blood sample analyzed for intracellular and extracellular levels of nutrients. In yet another non-limiting example, an element of user physiological data 124 may include a gut integrity measurement obtained from a microchip embedded under a user's skin. In yet another non-limiting example, an element of user physiological data 124 may include a stool sample analyzed for species of microbes and anaerobes. In an embodiment, one or more elements of user physiological data 124 may be organized within physiological database 120 such as by collection date and date of analysis, type of sample utilized to obtain a particular element of physiological data such as a microbiome sample or a saliva sample as described above in more detail in reference to FIG. 2.

With continued reference to FIG. 5, at step 515 a processor 104 identifies using at least an element of user physiological data 124 and a machine-learning algorithm 132 user constitutional enhancing food element 140 and user constitutional advancing food element 144. Machine-learning algorithm 132 may include any of the machine-learning algorithm 132 as described above in reference to FIG. 1. User constitutional enhancing food element 140 may include any of the user constitutional enhancing food element 140 as described above. User constitutional enhancing food element 140 may include food elements that are beneficial for a particular human being as described above in more detail in reference to FIG. 1. For instance and without limitation, machine-learning algorithm 132 may be utilized in combination with an element of user physiological data such as a saliva sample containing elevated estrone levels to identify user constitutional enhancing food element 140 such as cauliflower, cabbage, kale, garden cress, bok choy, broccoli, and brussels sprouts. User constitutional advancing food element 144 may include food elements not beneficial for a particular human being. For instance and without limitation, machine-learning algorithm 132 may be utilized in combination with an element of physiological data 124 such as a stool sample containing the presence of Clostridioides difficile to identify user constitutional advancing food element 144 such as alcohol, cabbage, kale, fried foods, black beans, and milk. Machine-learning algorithm 132 may be utilized in combination with an element of user physiological data 124 such as a hair sample containing high levels of arsenic to identify user constitutional enhancing food element 140 such as mussels, kale, dandelion, and spinach as well as to identify user constitutional advancing food element 144 such as fish, shrimp, shellfish, rice, and seaweed.

With continued reference to FIG. 5, identifying user constitutional enhancing food elements and user constitutional advancing food element 144 may include receiving physiological training data 128 wherein physiological training data 128 includes a plurality of pairs of physiological data 124 sets and constitutional enhancing food element 140 and constitutional advancing food element 144. Physiological training data may include any of the physiological training data 128 as described above in reference to FIG. 1. For example, physiological training data may include a plurality of physiological data 124 such as a plurality of sensor data containing blood pressure measurements containing constitutional enhancing food element 140 that include wild salmon, hazelnuts, black beans, and plain yogurt and constitutional advancing food element 144 that include pickles, jarred tomato sauce, salami, and frozen pizza. Processor 104 generates using a machine-learning algorithm 132 and physiological training data 128 a physiological model 136 correlating physiological data 124 with constitutional enhancing food element 140 and constitutional advancing food elements. Physiological model 136 may include any of the physiological model 136 s as described above in reference to FIG. 1. Physiological model may include performing a series of one or more calculations, algorithms, and/or equations. Generating a machine-learning algorithm 132 may include generating an unsupervised machine-learning algorithm including any of the unsupervised machine-learning algorithm as described above in reference to FIG. 1. Generating a machine-learning algorithm may include generating an unsupervised machine-learning algorithm including any of the unsupervised machine-learning algorithm as described above in reference to FIG. 1. Generating a machine-learning algorithm 132 may include generating a lazy-learning algorithm including any of the lazy-learning algorithms as described above in reference to FIG. 1.

With continued reference to FIG. 5, at step 520 a processor 104 classifies using a food element classifier 148 a food element descriptor 112 as a function of identified user constitutional enhancing food element 140 and user constitutional advancing food element 144. Food element classifier 148 may generate a classification algorithm 152, and generate a classification algorithm 152 and may derive from training data a model for sorting inputs into categories or bins of data. Food element classifier 148 classifies a food element descriptor 112 utilizing identified user constitutional enhancing food elements and user constitutional advancing food element 144. In an embodiment, food element classifier 148 may utilize identified user constitutional enhancing food elements and user constitutional advancing food element 144 as training data to generate classification algorithm 152. Classifying a food element descriptor 112 include generating a classification algorithm 152 wherein the classification algorithm 152 utilizes a food element descriptor 112 as an input and outputs a user constitutional enhancing food element 140 classification label or a user constitutional advancing food element 144 classification label. Food element classification label 156 may include any of the classification labels as described above in reference to FIG. 1. Classification label may indicate whether a food element descriptor 112 contains a user constitutional enhancing food element 140 or a user constitutional advancing food element 144. Classification label may contain a description of a particular food element descriptor 112 as containing a Classification algorithm 152 may include any of the classification algorithm 152 as described above in reference to FIG. 1. Food element classifier 148 may generate one or more classification algorithm 152. Classification algorithm 152 may include a Naïve-bayes algorithm. Classification algorithm 152 may include a K-nearest neighbor algorithm. Processor 104 identifies using a classification algorithm 152 a food element descriptor 112 as a user constitutional enhancing food element 140 or a user constitutional advancing food element.

With continued reference to FIG. 5, food element classifier 148 may generate a classification algorithm 152 using learned behavior patterns of a user. For instance and without limitation, an element of physiological data 124 that contains a description of vigorous physical activity that the user routinely participates in may be utilized in a machine-learning algorithm 132 to generate a list of user constitutional enhancing food elements that contains one or more additional food elements that may be available to the user because of the additional vigorous physical activity that the user participated in. In such an instance, a food element descriptor 112 may be classified as a constitutional enhancing food element 140 instead of being classified as a constitutional advancing food element 144. In yet another non-limiting example, an element of physiological data 124 that contains a physically extracted sample that is within normal limits of reference ranges and does not indicate abnormal findings may be utilized by food element classifier 148 to generate a list of user constitutional enhancing food element 140 that contains one or more food elements classified as user constitutional enhancing food elements that may not be classified as constitutional enhancing food elements if the same element of physiological data 124 was not within normal limits of reference ranges and did not indicate normal findings.

With continued reference to FIG. 5, at step 525 a processor 104 displays on a graphical user interface 160 a constitutional enhancing food element 140 or a constitutional advancing food element 144. Processor 104 may display on a graphical user interface 160 utilizing any network methodology as described herein. Processor 104 may display on a graphical user interface 160 one or more food elements and/or ways to view one or more food elements utilizing any of the methodologies as described above in reference to FIGS. 3A-3D. In an embodiment, a processor 104 may display a message indicating a user should purchase a food element that has been classified as a constitutional enhancing food element. In an embodiment, a processor 104 may display a message indicating a user should not purchase food element that has been classified as a constitutional advancing food element 144. In an embodiment, information displayed on a graphical user interface may be 160 may additionally or alternatively be transmitted to the user client device 108 wherein the information may be displayed on a graphical user interface 160 located on the user client device 108.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
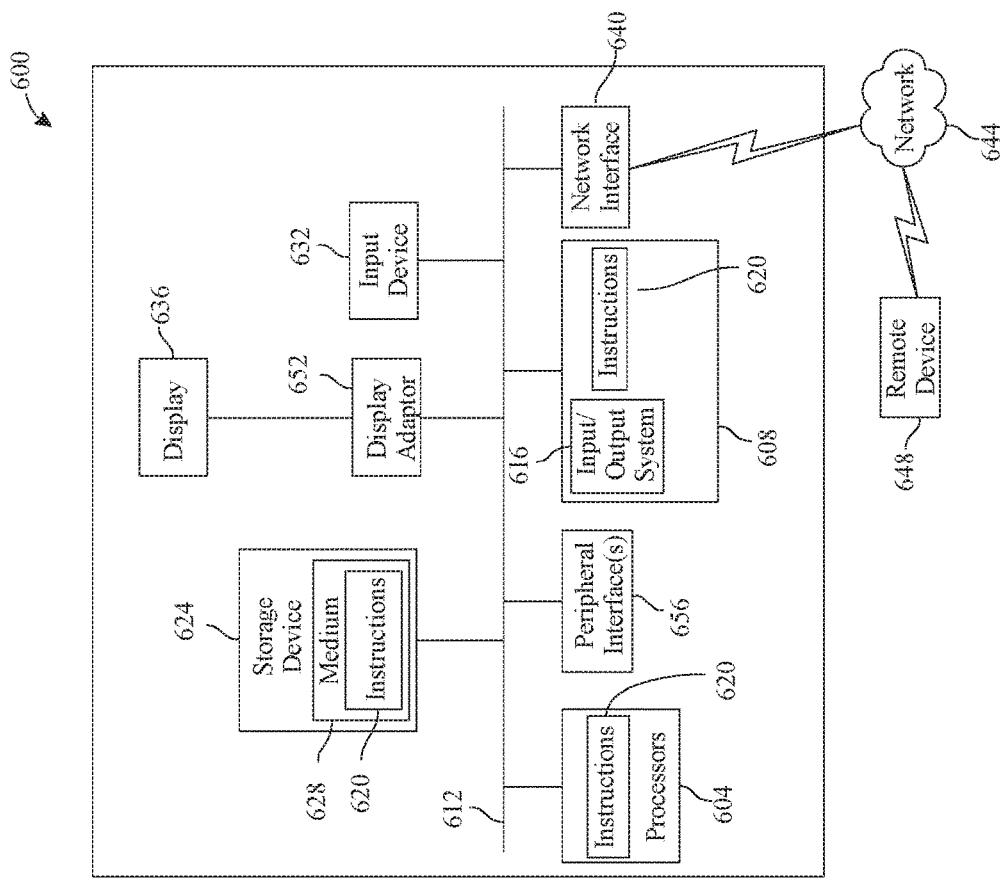
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for informing food element decisions in the acquisition of edible materials from any source, the system comprising a processor coupled to a memory, the processor is further configured to:

receive, from a user client device operated by a user, a food element descriptor wherein the food element descriptor further comprises a sequence uniquely identifying a particular food element; wherein the particular food element further comprises one or more ingredients; and wherein the one or more ingredients is selected based on a threshold importance score of ingredients based on user body information;

retrieve, by the processor from a physiological database, at least an element of user physiological data, said at least an element of user physiological data comprising a user nutrient body measurement;

identify, using the user nutrient body measurement and a machine-learning algorithm, a plurality of constitutional effect labels, each of the plurality of constitutional effect labels indicating one of a positive or negative effect on the user, wherein identifying the plurality of constitutional effect labels comprises:

receiving physiological training data wherein physiological training data further comprises physiological data and correlated to constitutional effect labels; and training, using the machine-learning algorithm and the physiological training data, a physiological model correlating physiological data with constitutional effect labels;

inputting the at least an element of user physiological data comprising the user nutrient body measurement into the physiological machine-learning model; and outputting, from the physiological machine-learning model, the plurality of constitutional effect labels as a function of the physiological machine-learning and the at least an element of user physiological data comprising the user nutrient body measurement;

generate a food element classifier, wherein the food element classifier comprises a classification algorithm, wherein the classification algorithm is trained by using training data comprising user physiological data sets of a plurality of users, the user physiological data sets comprising at least a nutrient body measurement of a user of the plurality of users, wherein the training data correlates the food element descriptor to the plurality of identified constitutional effect labels, and wherein responsive to training, the food element classifier is configured to provide an output of one or more constitutional effect labels of the food element description for a specific user responsive to an input of the nutrient body measurement of the specific user and the food element descriptor;

classify, using the food element classifier based at least on the nutrient body measurement of the specific user, the food element descriptor as a function of the plurality of constitutional effect labels; and display, by the processor on a graphical user interface for the specific user, the food element descriptor and a constitutional effect label for the food element descriptor, wherein the food element descriptor is displayed according to a food element category of the food element descriptor.

2. The system of claim 1, wherein the processor is further configured to receive, by the processor from an image capture device, a wireless transmission from the user client device containing a picture of a food element.

3. The system of claim 1, wherein the processor is further configured to receive, by the processor from an image capture device, a wireless transmission from the user client device containing a picture of a uniform code commission barcode.

4. The system of claim 1, wherein the machine-learning model further comprises executing a supervised machine-learning algorithm.

5. The system of claim 1, wherein the machine-learning model further comprises executing an unsupervised machine-learning algorithm.

6. The system of claim 1, wherein the machine-learning model further comprises executing a lazy-learning algorithm.

7. The system of claim 1, wherein the classification algorithm further comprises a Naive-Bayes classification algorithm.

8. The system of claim 1, wherein the classification algorithm further comprises a K-nearest neighbor algorithm.

9. A method of informing food element decisions in the acquisition of edible materials from any source, the method comprising:
- receiving, by a processor from a user client device operated by a user, a food element descriptor wherein the food element descriptor further comprises a sequence uniquely identifying a particular food element; wherein the particular food element further comprises one or more ingredients; and wherein the one or more ingredients is selected based on a threshold importance score of ingredients based on user body information;
- retrieving, by the processor from a physiological database at least an element of user physiological data, said at least an element of user physiological data comprising a user nutrient body measurement;
- identifying, by the processor using the user nutrient body measurement and a machine-learning algorithm, a plurality of constitutional effect labels, each of the plurality of constitutional effect labels indicating one of a positive or negative effect on the user, wherein identifying the plurality of constitutional effect labels comprises:
  - receiving physiological training data wherein physiological training data further comprises physiological data and correlated to constitutional effect labels; and
  - training, using the machine-learning algorithm and the physiological training data, a physiological model correlating physiological data with constitutional effect labels;
  - inputting the at least an element of user physiological data comprising the user gut-wall body characteristic measurement into the physiological machine-learning model; and
  - outputting, from the physiological machine-learning model, the plurality of constitutional effect labels as a function of the physiological machine-learning and the at least an element of user physiological data comprising the user nutrient body measurement;
- generating, by the processor, a food element classifier, wherein the food element classifier comprises a classification algorithm, wherein the classification algorithm is trained by using training data comprising user physiological data sets of a plurality of users, the user physiological data sets comprising at least a nutrient body measurement of a user of the plurality of users, wherein the training data correlates the food element descriptor to the plurality of identified constitutional effect labels, and wherein responsive to training, the food element classifier is configured to provide an output of one or more constitutional effect labels of the food element description for a specific user responsive to an input of the nutrient body measurement of the specific user and the food element descriptor;
- classifying, by the processor using the food element classifier based at least on the nutrient body measurement of the specific user, the food element descriptor as a function of the plurality of constitutional effect labels; and
- displaying, by the processor on a graphical user interface for the specific user, the food element descriptor and a constitutional effect label for the food element descriptor, wherein the food element descriptor is displayed according to a food element category of the food element descriptor.

10. The method of claim 9, wherein receiving the food element descriptor further comprises receiving a wireless transmission from the user client device containing a picture of a food element.

11. The method of claim 9, wherein receiving the food element descriptor further comprises receiving a wireless transmission from the user client device containing a picture of a uniform code commission barcode.

12. The method of claim 9, wherein generating the machine-learning algorithm further comprises executing a supervised machine-learning algorithm.

13. The method of claim 9, wherein generating the machine-learning algorithm further comprises executing an unsupervised machine-learning algorithm.

14. The method of claim 9, wherein generating the machine-learning algorithm further comprises executing a lazy-learning algorithm.

15. The method of claim 9, wherein generating the classification algorithm further comprises a Naïve-Bayes classification algorithm.

16. The method of claim 9, wherein generating the classification algorithm further comprises a K-nearest neighbor algorithm.

17. The system of claim 1, wherein the processor is further configured to display, by the processor on the graphical user interface for the specific user, at least a previous user behavior, wherein the at least a previous user behavior comprises: a previous food element descriptor that had been received from the user;
and a constitutional effect label for the previous food element descriptor.

18. The method of claim 9, further comprising displaying by the processor on the graphical user interface for the specific user, at least a previous user behavior, wherein the at least a previous user behavior comprises:
- a previous food element descriptor that had been received from the user; and
- a constitutional effect label for the previous food element descriptor.

* * * * *